United States Patent
Yoon (10) Patent No.: US 9,629,593 B2
(45) Date of Patent: Apr. 25, 2017

(54) METHOD OF CONTROLLING IMAGE DIAGNOSIS APPARATUS AND MOBILE TERMINAL FOR THE SAME, AND METHOD OF OPERATING IMAGE DIAGNOSIS APPARATUS AND IMAGE DIAGNOSIS APPARATUS FOR THE SAME

(71) Applicant: SAMSUNG MEDISON CO., LTD., Hongcheon-gun, Gangwon-do (KR)

(72) Inventor: Seung-il Yoon, Gangwon-do (KR)

(73) Assignee: SAMSUNG MEDISON CO., LTD., Hongcheon-Gun, Gangwon-Do (KR)

(*) Notice: Subject to any disclaimer, the term of this patent is extended or adjusted under 35 U.S.C. 154(b) by 12 days.

(21) Appl. No.: 14/380,330

(22) PCT Filed: Feb. 4, 2013

(86) PCT No.: PCT/KR2013/000867
§ 371 (c)(1),
(2) Date: Aug. 21, 2014

(87) PCT Pub. No.: WO2013/125801
PCT Pub. Date: Aug. 29, 2013

(65) Prior Publication Data
US 2015/0015379 A1    Jan. 15, 2015

(30) Foreign Application Priority Data
Feb. 22, 2012  (KR) .................. 10-2012-0018054

(51) Int. Cl.
G08C 17/02    (2006.01)
A61B 6/00     (2006.01)
(Continued)

(52) U.S. Cl.
CPC ............ *A61B 6/4405* (2013.01); *A61B 6/461* (2013.01); *A61B 6/467* (2013.01); *A61B 6/54* (2013.01);
(Continued)

(58) Field of Classification Search
CPC ...... G08C 17/02; G08C 2201/30; H04B 7/26; H04B 1/69; G06F 3/04886;
(Continued)

(56) References Cited

U.S. PATENT DOCUMENTS

| 8,523,433 B2* | 9/2013 | Butzine .......... A61B 6/4405 378/115 |
| 2002/0091659 A1* | 7/2002 | Beaulieu ........ G06F 19/321 706/62 |

(Continued)

FOREIGN PATENT DOCUMENTS

| EP | 1 681 031 A1 | 7/2006 |
| EP | 2 389 863 A1 | 11/2011 |

(Continued)

OTHER PUBLICATIONS

A. Aragues et al., "Trends and Challenges of the Emerging Technologies toward Interoperability and Standardization in e-Health Communications," IEEE Communications Magazine, IEEE Service Center, vol. 49, No. 11, Nov. 1, 2011, pp. 182-188.
(Continued)

*Primary Examiner* — Thomas Alunkal
(74) *Attorney, Agent, or Firm* — McDermott Will & Emery LLP (57) ABSTRACT

A method of controlling an image diagnosis apparatus by using a mobile terminal. The method includes: receiving identification information of the image diagnosis apparatus from the image diagnosis apparatus via a Wi-Fi direct (WFD) network or an ultra wideband (UWB) network;
(Continued)

displaying a virtual key pad corresponding to the received identification information of the image diagnosis apparatus; receiving a control command from the outside through the virtual key pad; and transmitting the received control command to the image diagnosis apparatus via the WFD or UWB network.

8 Claims, 4 Drawing Sheets

(51) Int. Cl.
    *H04W 12/06* (2009.01)
    *G06F 19/00* (2011.01)
    *G06F 3/0488* (2013.01)
    *H04B 1/69* (2011.01)
    *H04B 7/26* (2006.01)
    *A61B 8/00* (2006.01)
    *H04W 84/12* (2009.01)

(52) U.S. Cl.
    CPC ............ *A61B 6/563* (2013.01); *A61B 8/4427* (2013.01); *A61B 8/462* (2013.01); *A61B 8/467* (2013.01); *A61B 8/54* (2013.01); *A61B 8/565* (2013.01); *G06F 3/04886* (2013.01); *G06F 19/3418* (2013.01); *G08C 17/02* (2013.01); *H04B 1/69* (2013.01); *H04B 7/26* (2013.01); *H04W 12/06* (2013.01); *G08C 2201/30* (2013.01); *H04W 84/12* (2013.01)

(58) Field of Classification Search
    CPC ....... G06F 19/3418; A61B 8/54; A61B 8/565; A61B 6/4405; A61B 6/461; A61B 6/54; A61B 6/563; A61B 8/4427
    USPC ............................ 340/12.5, 539.12; 345/173
    See application file for complete search history.

(56) References Cited

U.S. PATENT DOCUMENTS

| | | | |
|---|---|---|---|
| 2004/0086164 A1* | 5/2004 | Moriyama | A61B 6/465 382/131 |
| 2004/0098167 A1 | 5/2004 | Yi et al. | |
| 2004/0100376 A1 | 5/2004 | Lye et al. | |
| 2005/0054923 A1* | 3/2005 | Pan | A61B 5/0002 600/437 |
| 2005/0149578 A1* | 7/2005 | Sustman | G06F 11/1464 |
| 2009/0182228 A1 | 7/2009 | Pierce | |
| 2010/0076789 A1* | 3/2010 | Pan | A61B 5/0002 705/3 |
| 2011/0049370 A1* | 3/2011 | Yoshida | A61B 6/4405 250/354.1 |
| 2012/0001853 A1* | 1/2012 | Tanaka | G06F 3/04886 345/168 |
| 2012/0030604 A1 | 2/2012 | Kim et al. | |
| 2013/0335408 A1* | 12/2013 | Yi | G06T 17/00 345/419 |

FOREIGN PATENT DOCUMENTS

| | | | |
|---|---|---|---|
| EP | 2389863 A1 * | 11/2011 | ........... A61B 6/4405 |
| KR | 10-2005-0086556 A | 8/2005 | |
| KR | 10-0542340 B1 | 1/2006 | |
| KR | 10-2009-0128962 A | 12/2009 | |
| KR | 10-2010-0025769 A | 3/2010 | |
| KR | 10-2012-0051477 A | 5/2010 | |
| KR | 10-2012-0011139 A | 2/2012 | |

OTHER PUBLICATIONS

Extended European Search Report issued in Application No. 13751523.5 dated Aug. 10, 2015.
International Search Report and Written Opinion of the International Searching Authority PCT/KR2013/000867 dataed Jun. 10, 2013.
Notice of Non-Final Rejection Korean Patent Application No. 10-2012-0018054 dated Jun. 28, 2013 with English translation.
Notice of Allowance Korean Patent Application No. 10-2012-0018054 dated Dec. 20, 2013 with English translation.

* cited by examiner

METHOD OF CONTROLLING IMAGE DIAGNOSIS APPARATUS AND MOBILE TERMINAL FOR THE SAME, AND METHOD OF OPERATING IMAGE DIAGNOSIS APPARATUS AND IMAGE DIAGNOSIS APPARATUS FOR THE SAME

TECHNICAL FIELD

The present invention relates to a method of controlling an image diagnosis apparatus by a mobile terminal by using a Wi-Fi direct (WFD) technology or an ultra wideband (UWB) technology, and more particularly, to a method of operating an image diagnosis apparatus controlled by the mobile terminal.

BACKGROUND ART

At present, most medical institutions construct a local private network to communicate between two devices. However, in terms of WiFi, in order to send/receive data between two devices, the devices need to access the same local private network (for example, an access point), and thus a medical institution needs to include a wireless network system. Meanwhile, when a public internet protocol (IP) address is used, both devices need to use an external server.

In terms of Bluetooth, a pairing procedure is required to connect two devices. The paring refers to a state where a communication linkage is allowed between two devices supporting a Bluetooth function. Also, when a plurality of devices that support a Bluetooth function exist near a user, there is an inconvenience in that the user needs to select devices to be connected to each other.

Accordingly, a system capable of easily connecting another mobile device to medical equipment and remotely controlling the medical equipment through the mobile device is required.

DISCLOSURE OF INVENTION

Solution to Problem

The present invention provides a method of controlling an image diagnosis apparatus using Wi-Fi direct (WFD) or ultra wideband (UWB) communication technology that may separate an input unit for control and an output unit for outputting an image from the image diagnosis apparatus and may remotely control the image diagnosis apparatus through a mobile terminal, and a method of operating the image diagnosis apparatus.

Advantageous Effects of Invention

According to the current embodiment, the mobile terminal may be used as an input/output unit of the image diagnosis apparatus, and thus the image diagnosis apparatus may be miniaturized. The image diagnosis apparatus may be configured as a multilayer including a plurality of image diagnosis apparatuses. Accordingly, many image diagnosis apparatuses may be used in a small space.

Also, since a user may remotely control the image diagnosis apparatus by using a WFD or UWB communication technology, there is no need to move the image diagnosis apparatus to another place where an object exists.

BRIEF DESCRIPTION OF DRAWINGS

The above and other features and advantages of the present invention will become more apparent by describing in detail exemplary embodiments thereof with reference to the attached drawings in which.

BEST MODE FOR CARRYING OUT THE INVENTION

According to an aspect of the present invention, there is provided a method of controlling an image diagnosis apparatus by using a mobile terminal, the method including: receiving identification information of the image diagnosis apparatus from the image diagnosis apparatus via a Wi-Fi direct (WFD) network or an ultra wideband (UWB) network; displaying a virtual key pad corresponding to the received identification information of the image diagnosis apparatus; receiving a control command from the outside through the virtual key pad; and transmitting the received control command to the image diagnosis apparatus via the WFD or UWB network.

The receiving of the identification information of the image diagnosis apparatus may include receiving identification information of a plurality of image diagnosis apparatuses from the plurality of image diagnosis apparatuses.

The displaying of the virtual key pad may include: displaying the identification information of the plurality of image diagnosis apparatuses; selecting one identification information from among the displayed identification information of the plurality of image diagnosis apparatuses; and displaying a virtual key pad corresponding to the selected identification information.

The virtual key pad varies according to a mode that is set in the image diagnosis apparatus.

The plurality of image diagnosis apparatuses may include at least two image diagnosis apparatuses that obtain images of different objects.

The method may further include receiving an examination image from the image diagnosis apparatus via the WFD or UWB network; and displaying the received examination image.

The method may further include transmitting the received examination image to a server.

According to another aspect of the present invention, there is provided a method of operating an image diagnosis apparatus, the method including: transmitting identification information of the image diagnosis apparatus to a mobile terminal via a Wi-Fi direct (WFD) network or an ultra wideband (UWB) network; receiving a control command from the mobile terminal via the WFD or UWB network; and performing the received control command.

The performing of the control command may include: obtaining an examination image of an object; and transmitting the obtained examination image to the mobile terminal via the WFD or UWB network.

The transmitting of the identification information of the image diagnosis apparatus may include: certifying authority of the mobile terminal to control the image diagnosis apparatus; and selectively transmitting identification information of the image diagnosis apparatus to the mobile terminal based on a result of the certification.

According to another aspect of the present invention, there is provided a mobile terminal including: a communication unit for receiving identification information of an the image diagnosis apparatus from the image diagnosis apparatus via a Wi-Fi direct (WFD) network or an ultra wideband (UWB) network and transmitting an input control command to the image diagnosis apparatus via the WFD or UWB network; a display unit for displaying a virtual key pad corresponding to the received identification information of the image diagnosis apparatus; a user input unit for receiving a control command from the outside through the virtual key pad; and a control unit for controlling the communication unit, the display unit, and the user input unit.

The communication unit receives identification information of a plurality of image diagnosis apparatuses from the plurality of image diagnosis apparatuses.

The display unit displays the identification information of the plurality of image diagnosis apparatuses and a virtual key pad corresponding to selected identification information; and the user input unit receives an input selecting one of the displayed identification information of the plurality of image diagnosis apparatuses.

The communication unit receives an examination image from the image diagnosis apparatus via the WFD or UWB network, and the display unit displays the received examination image.

The communication unit transmits the received examination image to a server.

According to another aspect of the present invention, there is provided an image diagnosis apparatus including: a communication unit for transmitting identification information of the image diagnosis apparatus to a mobile terminal via a Wi-Fi direct (WFD) network or an ultra wideband (UWB) network and receiving a control command from the mobile terminal via the WFD or UWB network; and a control unit for performing the received control command.

The image diagnosis apparatus may further include an image obtaining unit for obtaining an examination image of an object, wherein the communication unit transmits the obtained examination image to the mobile terminal via the WFD or UWB network.

The image diagnosis apparatus may further include a certification unit for certifying authority of the mobile terminal controlling the image diagnosis apparatus, wherein the communication unit selectively transmits identification information of the image diagnosis apparatus to the mobile terminal based on a result of the certification.

According to another aspect of the present invention, there is provided a computer readable recording medium having embodied thereon a computer program for executing the method.

According to another aspect of the present invention, there is provided a computer readable recording medium having embodied thereon a computer program for executing the method.

MODE FOR THE INVENTION

This application claims the benefit of Korean Patent Application No. 10-2012-0018054, filed on Feb. 22, 2012, in the Korean Intellectual Property Office, the disclosure of which is incorporated herein in its entirety by reference.

The present invention will now be described more fully with reference to the accompanying drawings, in which exemplary embodiments of the invention are shown.

Terms used hereinafter are used in consideration of the functions of the present invention and may be changed according to a user's or operator's intention, usual practice, or developments in new technology. Also, some terms may be arbitrarily selected by the applicant, and in this case, the meaning of the terms will be explained in detail. Accordingly, the terms will be defined based on the entire content of the description of the present invention.

Unless otherwise noted, the term "comprise" or variations such as "comprises" or "comprising" is understood to mean "includes, but is not limited to" so that other elements that are not explicitly mentioned may also be included. Also, the term "unit" or "module" means a unit performing at least one function and may operate by using hardware or software or a combination of hardware and software.

The term "examination image" herein means an image of an object obtained by using ultrasound, X-RAY, high frequency radiation, or the like. The object may be a body part. For example, examples of the object may include an organ such as a liver, a heart, a womb, a brain, a breast, or an abdomen, or an embryo.

When an examination image is an ultrasound image, the ultrasound image may be embodied in various ways. For example, the ultrasound image may be at least one of a brightness (B) mode image, a color (C) mode image, and a Doppler (D) mode image. Also, according to an embodiment of the present invention, the ultrasound image may be a two-dimensional (2D) image or a three-dimensional (3D) image.

The term "user" herein is, but is not limited to, a medical expert such as a surgeon, a nurse, a clinical pathologist, or a medical image expert.

Hereinafter, the present invention will be described more fully with reference to the accompanying drawings, in which exemplary embodiments of the invention are shown. The invention may, however, be embodied in many different forms and should not be construed as being limited to the embodiments set forth herein. When publicly known techniques or structures related to the present invention may unnecessarily make the present invention unclear, a detailed description thereof will be omitted. Similar elements are denoted by similar reference numerals throughout. Expressions such as "at least one of," when preceding a list of elements, modify the entire list of elements and do not modify the individual elements of the list.

Figure 1:
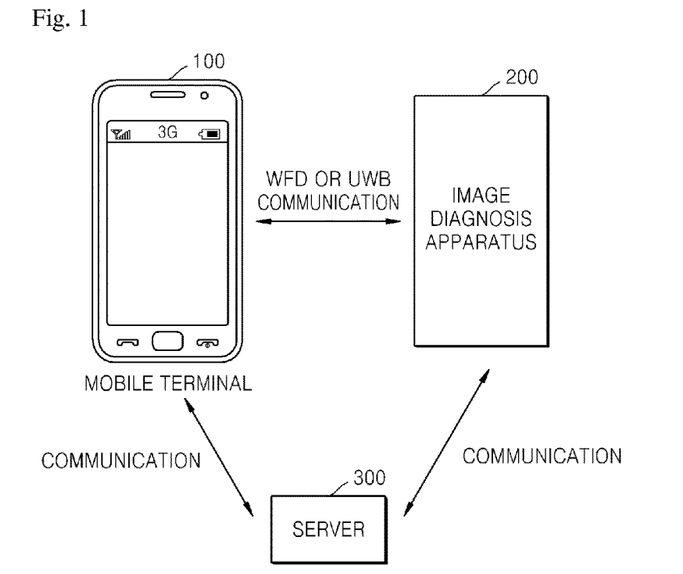
FIG. 1 is a block diagram of a system for controlling an image diagnosis apparatus according to an embodiment of the present invention.

FIG. 1 is a block diagram of a system for controlling an image diagnosis apparatus according to an embodiment of the present invention.

As shown in FIG. 1, a medical image providing system of the current embodiment may include a mobile terminal 100, an image diagnosis apparatus 200, and a server 300.

The mobile terminal 100 may be a terminal used by a medical image expert such as a surgeon, a nurse, or a clinical pathologist. According to the current embodiment, a user may input a control command or may obtain an examination image obtained by the image diagnosis apparatus 200 by using the mobile terminal 100. In other words, the user may use the mobile terminal 100 as an input/output unit of the image diagnosis apparatus 200.

The mobile terminal 100 may be embodied in various ways. For example, examples of the mobile terminal 100 may include a mobile phone, a smart phone, a personal digital assistant (PDA), a portable multimedia player (PMP), a navigation device, an e-book terminal, a tablet personal computer (PC), and the like.

The mobile terminal 100 may perform Wi-Fi direct (WFD) or ultra wideband (UWB) communication. Accordingly, according to the current embodiment, the mobile terminal 100 may send/receive data to/from the image diagnosis apparatus 200 by using a WFD or UWB network.

The WFD is a new version of a Wi-Fi technology and has a main characteristic that enables direct communication between devices. That is, if there is a device in which WFD is installed, devices may communicate share information with each other without a hot spot, a router, or an access point (AP). Also, the WFD does not need to perform a pairing procedure as in Bluetooth, enables telecommunication up to about 200m at most, and enables 1:N communication with a plurality of devices.

The UWB is a wireless transmission technology which transmits a large amount of digital data at low power through a wide spectrum frequency within a short distance range.

Meanwhile, the mobile terminal 100 may perform wireless communication with the server 300. Accordingly, the mobile terminal 100 may transmit data obtained from the image diagnosis apparatus 200 to the server 300.

The image diagnosis apparatus 200 refers to an apparatus capable of obtaining a medical image of an object to aid in medical treatment. Examples of the image diagnosis apparatus 200 may include a magnetic resonance imaging (MRI) apparatus, ultrasound diagnostic equipment, a computed tomography (CT) apparatus, an X-ray diagnosis apparatus, and the like, but the present invention is not limited thereto.

According to the current embodiment, the image diagnosis apparatus 200 may be configured as one package including a plurality of image diagnosis apparatuses 200. The plurality of image diagnosis apparatuses 200 may be the same kind of image diagnosis apparatuses or different kinds of image diagnosis apparatuses.

The image diagnosis apparatus 200 may perform WFD or UWB communication. Accordingly, the image diagnosis apparatus 200 may transmit an examination image to the mobile terminal 100 via a WFD or UWB network.

The image diagnosis apparatus 200 may perform wired or wireless communication with the server 300. A structure of the image diagnosis apparatus 200 will be described later with reference to FIG. 3.

The server 300 is a server for providing a medical service, and may be, for example, a medical institution server.

The server 300 may store object information including an object and identification information (ID, a resident registration number, a name, an address, contact information, etc.), examination image information regarding the object obtained by the image diagnosis apparatus 200, diagnosis result information of the object, and the like.

According to the current embodiment, the server 300 may be connected to at least one of the mobile terminal 100 and the image diagnosis apparatus 200 via a network. Accordingly, the server 300 may send/receive data to/from the mobile terminal 100 or the image diagnosis apparatus 200.

Hereinafter, a structure of the mobile terminal 100 will be described in detail with reference to FIG. 2.

Figure 2:
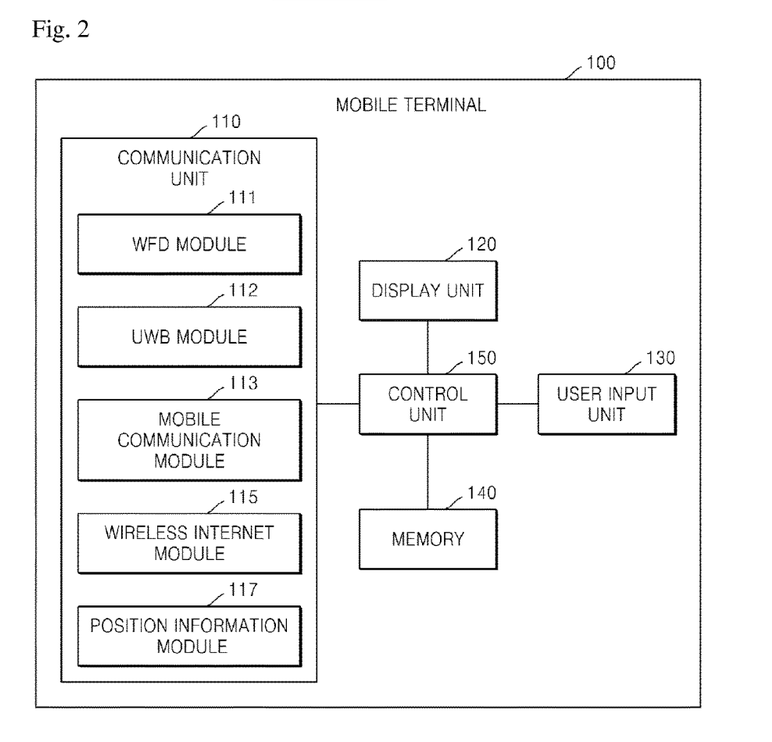
FIG. 2 is a block diagram of a mobile terminal according to an embodiment of the present invention.

FIG. 2 is a block diagram of a mobile terminal according to an embodiment of the present invention.

As shown in FIG. 2, the mobile terminal 100 may include a communication unit 110, a display unit 120, a user input unit 130, a memory 140, and a control unit 150. However, all components shown in FIG. 2 are not essential components. The mobile terminal 100 may include more or less components than the components shown in FIG. 2.

The communication unit 110 may include at least one component that communicates with the image diagnosis apparatus 200 or the server 300. For example, the communication unit 110 may include a WFD module 111, a UWB module 112, a mobile communication module 113, a wireless internet module 115, a position information module 117, and the like.

The WFD module 111 refers to a module for performing Wi-Fi direct communication. The UWB module 112 refers to a module for performing ultra-wideband communication. According to the current embodiment, the WFD module 111 or the UWB module 112 may receive identification information of the image diagnosis apparatus 200 via a WFD or UWB network. The identification information of the image diagnosis apparatus 200 may include a serial number, an identification code, etc. of the image diagnosis apparatus 200.

In this case, according to the current embodiment, the WFD module 111 or the UWB module 112 may receive identification information of a plurality of the image diagnosis apparatuses 200.

Also, the WFD module 111 or the UWB module 112 may transmit a control command that is input by a user to the image diagnosis apparatus 200 via a WFD or UWB network. The control command according to the current embodiment may include a command for obtaining an examination image, a command for converting a mode, a command for transmitting the obtained examination image with respect to an object, and the like.

Meanwhile, the WFD module 111 or the UWB module 112 may receive an examination image from the image diagnosis apparatus 200 via a WFD or UWB network. The examination image may be an examination image that is previously stored or an examination image that is obtained in real time.

The mobile communication module 113 may send/receive a wireless signal to/from at least one of a base station, an external terminal, and the server 300 via a mobile communication network. In this regard, the wireless signal may include various types of data according to sending/receiving of an examination image.

The wireless internet module 115 refers to a module for wireless internet connection and may be internally or externally formed.

The position information module 117 refers to a module for determining or obtaining a position of the mobile terminal 100. For example, the position information module 117 may be a global position system (GPS) module. The GPS module receives position information from a plurality of satellites. In this regard, the position information may include coordinate information represented by longitudes and latitudes.

The communication unit 110 may transmit the examination image received from the image diagnosis apparatus 200 to the server 300. In this case, the communication unit 110 may transmit the examination image to the server 300 by using the mobile communication module 113 or the wireless internet module 115.

Accordingly, according to the current embodiment, even though network connection of the image diagnosis apparatus 200 is not possible, the image diagnosis apparatus 200 may transmit the obtained examination image to the server 300 via the mobile terminal 100.

The display unit 120 displays and outputs information that is processed by the mobile terminal 100. For example, the display unit 120 may display identification information of the image diagnosis apparatus 200 that is received from the image diagnosis apparatus 200. If identification information regarding the image diagnosis apparatus 200 is received, the display unit 120 may output the identification information regarding the image diagnosis apparatus 200 in the form of a list.

The display unit 120 may display a virtual key pad corresponding to the identification information regarding the image diagnosis apparatus 200. The virtual key pad refers to a group of input keys that are required to represent a specific language or to control a specific mode or a specific menu of the image diagnosis apparatus 100.

According to the current embodiment, the display unit 120 may display the examination image received from the image diagnosis apparatus 200 or the server 300.

The display unit 120 may include at least one of a liquid crystal display (LCD), a thin film transistor-liquid crystal display (TFT-LCD), an organic light-emitting diode (OLED), a flexible display, and a 3D display. There may be at least two display units 120 according to a type of the mobile terminal 100 that is embodied.

The user input unit 130 generates input data for controlling operations of the mobile terminal 100. The user input unit 130 may be configured as a key pad, a dome switch, a touch pad (pressure/electrostatic), a jog wheel, a jog switch, or the like. In particular, when the touch pad and the display unit 120 form a layered structure, this may be called a touch screen.

According to the current embodiment, when the display unit 120 and the touch pad form a touch screen, the display unit 120 may be used as an input unit as well as an output unit. In other words, the display unit 120 and the user input unit 130 may be configured as one body.

The touch screen may be formed to detect touch input pressure as well as a touch input position, on a touched area. Also, the touch screen may be formed to detect a proximity touch as well as a real-touch.

According to the current embodiment, the user input unit 130 may receive a control command from the outside via the displayed virtual key pad. In other words, a user may input a control command with respect to the image diagnosis apparatus 200 by using the virtual key pad displayed on the display unit 120 of the mobile terminal 100.

According to the current embodiment, when identification information of the plurality of image diagnosis apparatuses 200 are displayed, a user may select one of the displayed identification information of the plurality of image diagnosis apparatuses 200 by using the user input unit 130. In other words, the user may select the image diagnosis apparatus 200 to be controlled by using the user input unit 130.

The memory 140 may store a program for processing and controlling the control unit 150 and may perform a function for temporarily storing input/output data (for example, an examination image, diagnosis result information, etc.).

The memory 140 may include at least one storage medium from among a flash memory type memory, a multimedia card micro type memory, a card type memory (for example, a secure digital (SD) memory, an extreme digital (XD) memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disc, and an optical disc. Also, the mobile terminal 100 may operate a web storage for performing a storage function of the memory 140 on the Internet.

According to the current embodiment, the memory 140 may store identification information of the mobile terminal 100, user information (for example, user's ID, a certification code, or the like), virtual key pad information that is mapped with the image diagnosis apparatus 200, and the like.

The control unit 150 may generally control the communication unit 110, the display unit 120, the user input unit 130, and the memory 140.

Hereinafter, a structure of the image diagnosis apparatus 200 will be described in detail with reference to FIG. 3.

Figure 3:
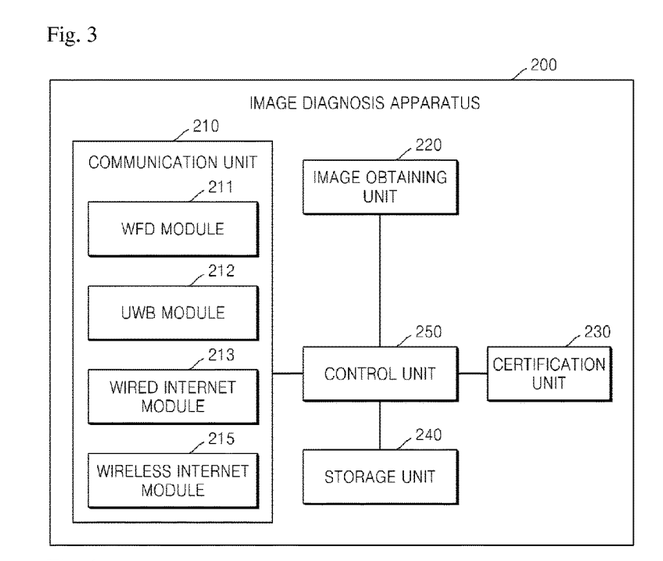
FIG. 3 is a block diagram of the image diagnosis apparatus of FIG. 1.

FIG. 3 is a block diagram of the image diagnosis apparatus 200 of FIG. 1.

As shown in FIG. 3, the image diagnosis apparatus 200 may include a communication unit 210, an image obtaining unit 220, a certification unit 230, a storage unit 240, and a control unit 250. However, all components shown in FIG. 3 are not essential components. The image diagnosis apparatus 200 may include more or less components than the components shown in FIG. 3.

The communication unit 210 may include at least one component that enables communication between the image diagnosis apparatus 200, the mobile terminal 100, and the server 300. For example, the communication unit 210 may include a WFD module 211, a UWB module 212, a wired internet module 213, a wireless internet module 215, and the like.

The WFD module 211 or the UWB module 212 may transmit identification information of the image diagnosis apparatus 200 to the mobile terminal 100 via a WFD or UWB network. In this regard, according to the current embodiment, the WFD module 211 or the UWB module 212 may receive identification information or certification information of the mobile terminal 100 via a WFD or UWB network to determine whether the mobile terminal 100 has authority to control the image diagnosis apparatus 200.

According to the current embodiment, when the mobile terminal 100 has authority to control the image diagnosis apparatus 200, the WFD module 211 or the UWB module 212 may receive a control command from the mobile terminal 100 via a WFD or UWB network.

Meanwhile, according to the current embodiment, the WFD module 211 or the UWB module 212 may transmit the obtained examination image of the object to the mobile terminal 100 via a WFD or UWB network.

The wired internet module 213 refers to a module for wired internet connection.

Also, the wireless internet module 215 refers to a module for wireless internet connection and may be internally or externally formed.

The communication unit 210 may transmit the examination image obtained by using the wired internet module 213 or the wireless internet module 215 to the server 300.

The image obtaining unit 220 may obtain an examination image of an object. According to the current embodiment, the image obtaining unit 220 may obtain the examination image based on the control command received from the mobile terminal 100. The examination image may be an ultrasound image, an MRI image, a CT image, or the like.

The examination image may include a plurality of images. In this case, the image obtaining unit 230 may obtain a plurality of examination images at a predetermined time interval.

The certification unit 230 may perform certification with respect to the mobile terminal 100. In other words, the certification unit 230 may certify whether the mobile terminal 100 has authority to control the image diagnosis apparatus 200.

The certification may be performed by using various methods. According to the current embodiment, the certification unit 230 may receive identification information from the mobile terminal 100 and determine whether the received identification information of the mobile terminal 100 is previously registered in a list of the mobile terminal 100 having authority to control the image diagnosis apparatus 200.

According to another embodiment of the present invention, the certification unit 230 may request the mobile terminal 100 for additional certification information. The certification information may be a user's ID, a password, and the like.

The storage unit 240 may store the obtained examination image. In this regard, the storage unit 240 may classify the examination image by patients and examination dates and may store the examination image.

According to the current embodiment, the storage unit 240 may store information of the mobile terminal 100. The information of the mobile terminal 100 may be identification information, control authority information of the mobile terminal 100, or the like.

The control authority information refers to authority information of the mobile terminal 100 that may control the image diagnosis apparatus 200 via a WFD or UWB network. In other words, only the mobile terminal 100 that is registered in the storage unit 240 and has control authority may be used as an input/output unit of the image diagnosis apparatus 200 via a WFD or UWB network.

According to the current embodiment, the storage unit 240 may be embedded in the image diagnosis apparatus 200 or may be configured as an external memory. Also, the storage unit 240 may be configured as a storage server.

The control unit 250 may execute the control command received from the mobile terminal 100. In other words, a user may transmit the control command to the image diagnosis apparatus 200 via the mobile terminal 100.

Also, the control unit 250 may generally control the communication unit 210, the image obtaining unit 220, the certification unit 230, the storage unit 240, and the control unit 250.

Hereinafter, a method of controlling the image diagnosis apparatus 200 by using the components of the mobile terminal 100 will be described in detail with reference to FIG. 4.

Figure 4:
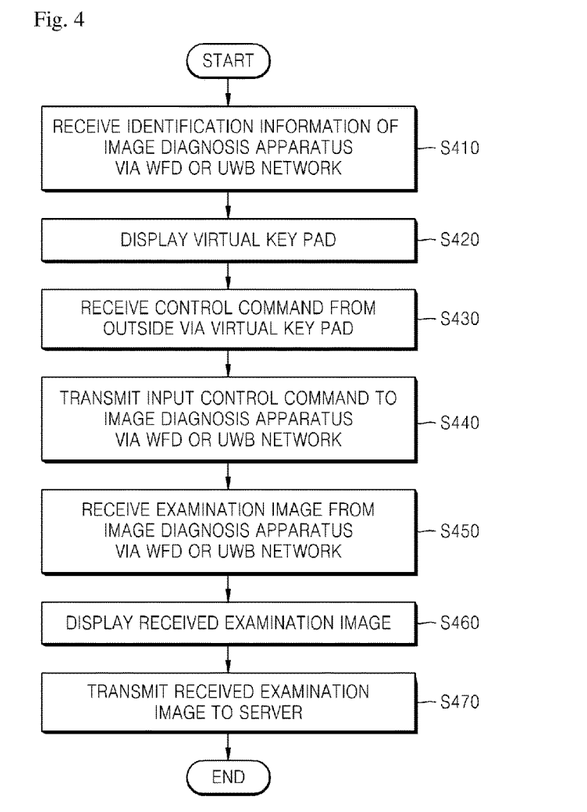
FIG. 4 is a flowchart for describing a method of controlling the image diagnosis apparatus of FIG. 1.

FIG. 4 is a flowchart for describing a method of controlling a method of controlling the image diagnosis apparatus 200 of FIG. 1.

The mobile terminal 100 may receive identification information of the image diagnosis apparatus 200 via a WFD or UWB network (operation S410). The identification information of the image diagnosis apparatus 200 may include a serial number, model information, an ID, and the like.

According to the current embodiment, the mobile terminal 100 may receive identification information from the plurality of image diagnosis apparatuses 200. There may be at least two image diagnosis apparatuses 200 that obtain images of different objects.

For example, the mobile terminal 100 may receive identification information of an ultrasound apparatus A for obtaining an ultrasound image of a liver and identification information of an ultrasound apparatus B for obtaining an ultrasound image of an embryo.

The mobile terminal 100 may display a virtual key pad corresponding to the received identification information of the image diagnosis apparatus 200 (operation S420). For example, when the image diagnosis apparatus 200 is a 'model A', the mobile terminal 100 may display a virtual key pad A, and when the image diagnosis apparatus 200 is a 'model B', the mobile terminal 100 may display a virtual key pad B.

Meanwhile, according to the current embodiment, when the identification information regarding the plurality of image diagnosis apparatuses 200 are received, the mobile terminal 100 may display the identification information regarding the plurality of image diagnosis apparatuses 200. The mobile terminal 100 may receive one of the displayed identification information regarding the plurality of image diagnosis apparatuses 200.

In other words, a user may determine the displayed identification information regarding the plurality of image diagnosis apparatuses 200 and select identification information to be controlled. In this case, the mobile terminal 100 may display a virtual key pad corresponding to identification information of the image diagnosis apparatus 200 that is selected by a user.

The mobile terminal 100 may receive a control command from the outside via the virtual key pad (operation S430). In other words, a user may input a control command to the mobile terminal 100 by using the displayed virtual key pad. For example, the user may change an image mode by using the virtual key pad and input a predetermined command, for example, to select the examination image.

According to the current embodiment, the mobile terminal 100 may display a virtual key pad corresponding to a menu or a mode in the image diagnosis apparatus 200. In other words, the virtual key pad may vary according to a mode that is set in the image diagnosis apparatus 200.

Accordingly, according to the current embodiment, the mobile terminal 100 may be used as an input/output unit of the image diagnosis apparatus 200, and the image diagnosis apparatus 200 is practical because a size of the image diagnosis apparatus 200 may be reduced.

The mobile terminal 100 may transmit the input control command to the image diagnosis apparatus 200 via the WFD or UWB network (operation S440). In this regard, according to the current embodiment, the mobile terminal 100 may transmit a command to obtain an examination image of an object to the image diagnosis apparatus 200 via the WFD or UWB network.

In this case, the mobile terminal 100 may receive the examination image from the image diagnosis apparatus 200 via the WFD or UWB network (operation S450). According to the current embodiment, the mobile terminal 100 may receive the examination image by downloading or streaming. Meanwhile, according to the current embodiment, the image diagnosis apparatus 200 may transmit the examination image in response to the request of the mobile terminal 100 and may transmit the examination image regardless of the request of the mobile terminal 100.

According to the current embodiment, the mobile terminal 100 may display the received examination image (operation S460). In this case, the mobile terminal 100 may decode the received examination image.

According to the current embodiment, even though the image diagnosis apparatus 200 is separated from an object or a user, the user may obtain an examination image of the object through a probe and may see the examination image obtained through the mobile terminal 100, and thus user convenience is increased.

Meanwhile, according to the current embodiment, the mobile terminal 100 may transmit the received examination image to the server 300 (operation S470). Accordingly, according to the current embodiment, even when the image diagnosis apparatus 200 may not communicate with the server 300, the mobile terminal 100 may receive the examination image via the WFD or UWB network and transmit the received examination image to the server 300.

Figure 5:
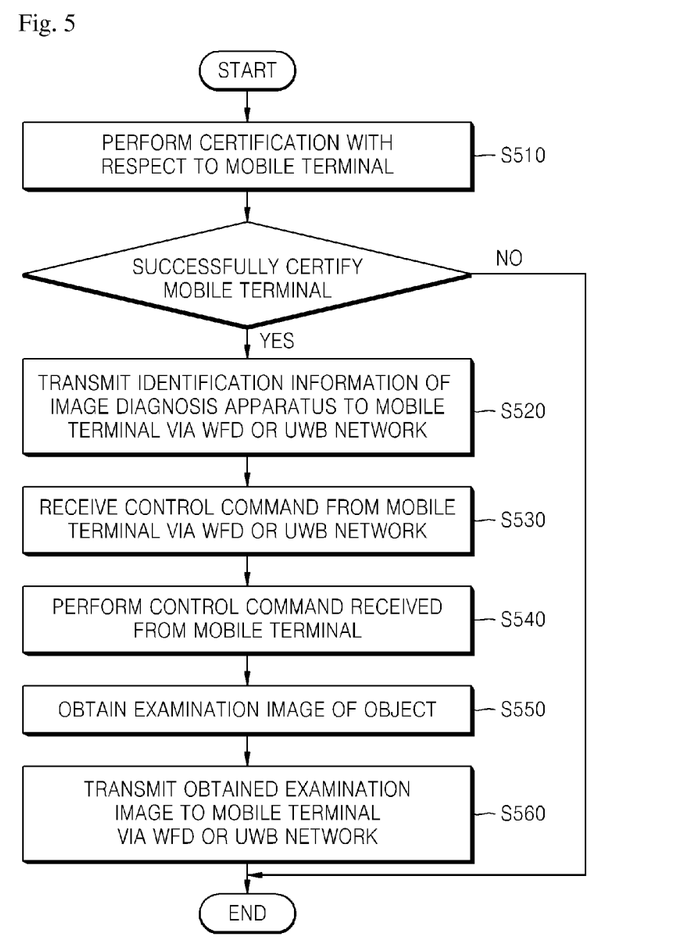
FIG. 5 is a flowchart for describing a method of operating the image diagnosis apparatus of FIG. 1.

FIG. 5 is a flowchart for describing a method of operating the image diagnosis apparatus 200 of FIG. 1.

According to the current embodiment, the image diagnosis apparatus 200 may perform certification with respect to the mobile terminal 100 (operation S510). In other words, the image diagnosis apparatus 200 may perform certification regarding whether the mobile terminal 100 has authority to control the image diagnosis apparatus 200.

According to the current embodiment, the image diagnosis apparatus 200 may perform certification based on the identification information (for example, an ID of the mobile terminal 100, a mobile number, a user's ID, etc.) of the mobile terminal 100 received via the WFD or UWB network.

For example, it is assumed that the identification information of the mobile terminal 100 capable of controlling the image diagnosis apparatus 200 is registered in a database of the image diagnosis apparatus 200. The image diagnosis apparatus 200 may determine whether the mobile terminal 100 has authority to control the image diagnosis apparatus 200 by ascertaining whether the received identification information of the mobile terminal 100 corresponds to the previously registered identification information of the mobile terminal 100.

As a result of the determination, when the mobile terminal 100 does not have authority to control the image diagnosis apparatus 200, the image diagnosis apparatus 200 may not provide identification information of the image diagnosis apparatus 200 to the mobile terminal 100. In this case, a user may not use the mobile terminal 100 as an input/output unit of the image diagnosis apparatus 200.

According to another embodiment of the present invention, the image diagnosis apparatus 200 may request the mobile terminal 100 for additional certification information. For example, the image diagnosis apparatus 200 may request the mobile terminal 100 for a personal identification number (PIN) via the WFD or UWB network. In this case, the image diagnosis apparatus 200 performs certification regarding authority of the mobile terminal 100 controlling the image diagnosis apparatus 200 based on the received user's personal identification information.

When the image diagnosis apparatus 200 succeeds in certifying the mobile terminal 100, the image diagnosis apparatus 200 may transmit the identification information of the image diagnosis apparatus 200 to the mobile terminal 100 via the WFD or UWB network (operation S520). In this regard, the mobile terminal 100 may display a virtual key pad for controlling the image diagnosis apparatus 200 based on the received identification information of the image diagnosis apparatus 200.

According to the current embodiment, the image diagnosis apparatus 200 may receive a control command from the mobile terminal 100 via the WFD or UWB network (operation S530). In this case, the image diagnosis apparatus 200 performs the control command received from the mobile terminal 100 (operation S540).

If the control command received from the mobile terminal 100 is a command for obtaining an examination image of an object, the image diagnosis apparatus 200 obtains the examination image of the object (operation S550). According to the current embodiment, the image diagnosis apparatus 200 may store the obtained examination image. Also, according to the current embodiment, the image diagnosis apparatus 200 may convert the obtained examination image into a Digital Imaging and Communications in Medicine (DICOM) file.

According to the current embodiment, if the control command received from the mobile terminal 100 is a command for transmitting an examination image, the image diagnosis apparatus 200 transmits the obtained examination image to the mobile terminal 100 via a WFD or UWB network (operation S560). In this regard, according to the current embodiment, the image diagnosis apparatus 200 may transmit an obtained screen to the mobile terminal 100 by using a real-time image streaming method.

Figure 6:
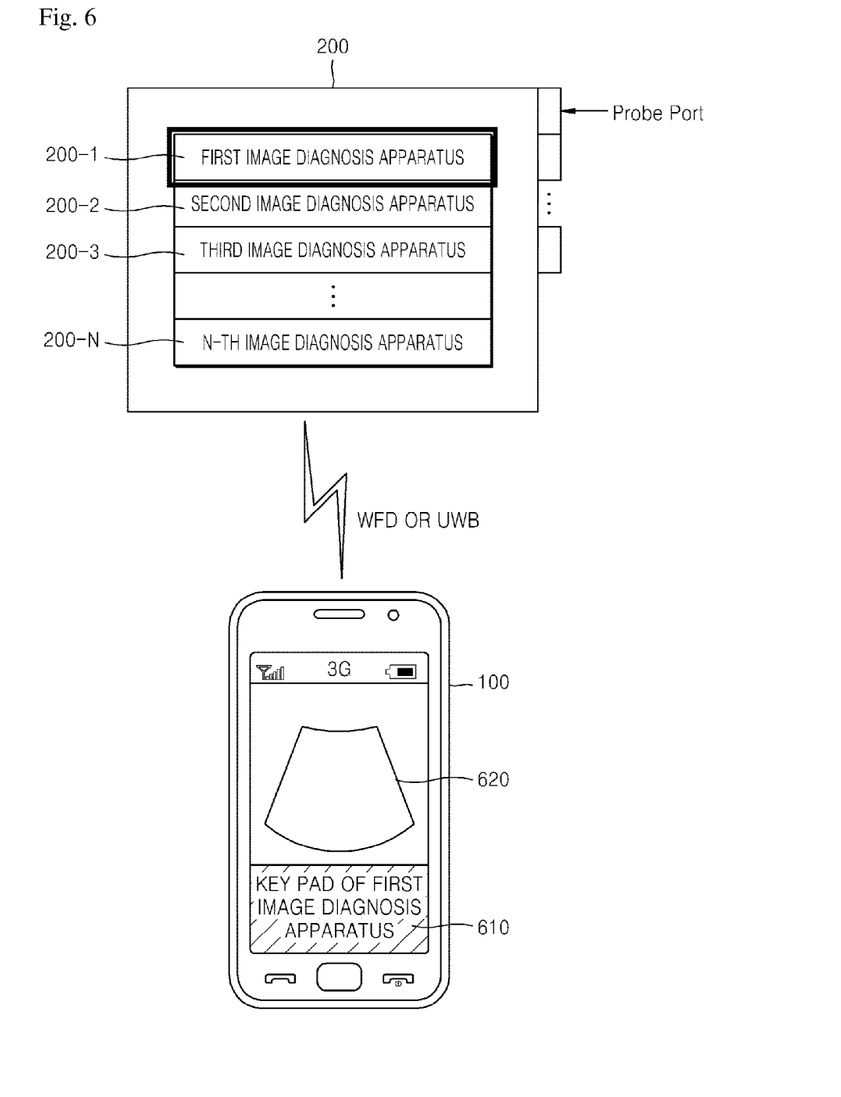
FIG. 6 is a view for describing a plurality of image diagnosis apparatuses according to an embodiment of the present invention.

FIG. 6 is a view for describing a plurality of image diagnosis apparatuses according to an embodiment of the present invention.

As shown in FIG. 6, the image diagnosis apparatus 200 may be configured as a package type including first to n-th image diagnosis apparatuses 200-1 to 200-N.

According to the current embodiment, the mobile terminal 100 may receive identification information regarding the first to n-th image diagnosis apparatuses 200-1 to 200-N. The mobile terminal 100 may display the identification information regarding the first to n-th image diagnosis apparatuses 200-1 to 200-N.

If a user selects the first image diagnosis apparatus 200-1, the mobile terminal 100 may perform WFD or UWB communication with the first image diagnosis apparatus 200-1, and the user may remotely control the first image diagnosis apparatus 200-1 by using the mobile terminal 100.

According to the current embodiment, the mobile terminal 100 may display a virtual key pad 610 with respect to the first image diagnosis apparatus 200-1. In this case, a user may input a control command with respect to the first image diagnosis apparatus 200-1 by using the virtual key pad 610.

Also, the mobile terminal 100 may receive and display an examination image 620 obtained by the first image diagnosis apparatus 200-1.

According to the current embodiment, the mobile terminal 100 may be used as an input/output unit of the image diagnosis apparatus 200, and thus the image diagnosis apparatus 200 may be miniaturized. The image diagnosis apparatus 200 may be configured as a multi-layer including a plurality of image diagnosis apparatuses as shown in FIG. 6. Accordingly, many image diagnosis apparatuses may be used in a small space.

Also, since a user may remotely control the image diagnosis apparatus 200 by using a WFD or UWB communication technology, there is no need to move the image diagnosis apparatus 200 to another place where an object exists.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of controlling an image diagnosis apparatus by using a mobile terminal, the method comprising:
   receiving identification information of a plurality of image diagnosis apparatuses from the plurality of image diagnosis apparatuses via a Wi-Fi direct (WFD) network or an ultra wideband (UWB) network;
   displaying the identification information comprising model information of each of the plurality of image diagnosis apparatuses;
   receiving a selection of identification information of a particular image diagnosis apparatus from among the displayed identification information of the plurality of image diagnosis apparatuses;
displaying a virtual key pad corresponding to the selected identification information of the particular image diagnosis apparatus;
receiving a control command from the outside through the virtual key pad; and
transmitting the received control command to the particular image diagnosis apparatus via the WFD or UWB network,
wherein the displaying the virtual key pad comprises:
displaying a first virtual key pad according to a first mode among a plurality of imaging operating modes of the particular image diagnosis apparatus;
receiving an input for selecting a second mode among the plurality of imaging operating modes;
changing the first virtual key pad to a second virtual key pad according to the selected second mode that is set in the particular image diagnosis apparatus, and displaying the second virtual key pad.

2. The method of claim 1, wherein the plurality of image diagnosis apparatuses comprise at least two image diagnosis apparatuses that obtain images of different objects.

3. The method of claim 1, further comprising:
receiving an examination image from the particular image diagnosis apparatus via the WFD or UWB network; and
displaying the received examination image.

4. The method of claim 3, further comprising transmitting the received examination image to a server.

5. A mobile terminal comprising:
a communicator configured to receive identification information of a plurality of image diagnosis apparatuses from the plurality of image diagnosis apparatuses via a Wi-Fi direct (WFD) network or an ultra wideband (UWB) network and transmitting an input control command to a particular image diagnosis apparatus from among the plurality of image diagnosis apparatuses via the WFD or UWB network;
a display configured to display the identification information comprising model information of each of the plurality of image diagnosis apparatuses, and display a virtual key pad corresponding to the identification information of the particular image diagnosis apparatus;
a user input device configured to receive a selection of identification information of a particular image diagnosis apparatus from among the displayed identification information of the plurality of image diagnosis apparatuses based on a user input, and receive a control command from the outside through the virtual key pad; and
controller configured to control the communicator, the display, and the user input unit device,
wherein the display displays a first virtual key pad according to a first mode among a plurality of imaging operating modes of the particular image diagnosis apparatus,
wherein the user input device receives an input for selecting a second mode among the plurality of imaging operating modes,
wherein the controller changes the first virtual key pad to a second virtual key pad varies according to the selected second mode that is set in the particular image diagnosis apparatus, and
wherein the display displays the second virtual key pad.

6. A non-transitory computer-readable recording medium having recorded thereon a program for executing the method of claim 1.

7. The method of claim 1, wherein the mobile terminal is at least one of a mobile phone, a smart phone, a personal digital assistant (PDA), a portable multimedia player (PMP), a navigation device, an e-book terminal, and a tablet personal computer (PC).

8. The method of claim 1, wherein the receiving identification information of a plurality of image diagnosis apparatuses comprises receiving identification information of the ultrasound apparatus A and identification information of the ultrasound apparatus B.

* * * * *